US010221390B2

(12) United States Patent
Shogbon et al.

(10) Patent No.: US 10,221,390 B2
(45) Date of Patent: *Mar. 5, 2019

(54) SYNTHETIC SURFACES FOR CULTURING STEM CELL DERIVED OLIGODENDROCYTE PROGENITOR CELLS

(71) Applicant: Asterias Biotherapeutics, Inc., Fremont, CA (US)

(72) Inventors: Christopher Bankole Shogbon, Corning, NY (US); Yue Zhou, Horseheads, NY (US); Ralph Brandenberger, Palo Alto, CA (US)

(73) Assignee: Asterias Biotherapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/452,710

(22) Filed: Mar. 7, 2017

(65) Prior Publication Data

US 2018/0023053 A1  Jan. 25, 2018

Related U.S. Application Data

(63) Continuation of application No. 14/997,999, filed on Jan. 18, 2016, which is a continuation of application No. 13/946,032, filed on Jul. 19, 2013, now Pat. No. 9,238,794, which is a continuation of application No. 12/362,250, filed on Jan. 29, 2009, now Pat. No. 8,513,009.

(60) Provisional application No. 61/063,010, filed on Jan. 30, 2008.

(51) Int. Cl.
*C12M 1/32* (2006.01)
*C12N 5/0797* (2010.01)
*C12N 5/00* (2006.01)
*C12N 5/079* (2010.01)

(52) U.S. Cl.
CPC ........... *C12N 5/0623* (2013.01); *C12M 23/12* (2013.01); *C12N 5/0068* (2013.01); *C12N 5/0622* (2013.01); *C12N 2500/90* (2013.01); *C12N 2506/02* (2013.01); *C12N 2533/30* (2013.01)

(58) Field of Classification Search
CPC .. C12N 5/0623; C12N 5/0068; C12N 5/0622; C12N 2500/90; C12N 2506/02; C12N 2533/30; C12M 23/12
See application file for complete search history.

(56) References Cited

U.S. PATENT DOCUMENTS

| | | |
|---|---|---|
| 3,502,545 A | 3/1970 | Westman et al. |
| 4,022,754 A | 5/1977 | Howes et al. |
| 4,578,079 A | 3/1986 | Ruoslahti et al. |
| 4,792,525 A | 12/1988 | Ruoslahti et al. |
| 4,908,236 A | 3/1990 | Pitt et al. |
| 5,278,063 A | 1/1994 | Hubbell et al. |
| 5,330,911 A | 7/1994 | Hubbell et al. |
| 5,480,953 A | 1/1996 | Sugaya et al. |
| 5,643,561 A | 7/1997 | Katsuen et al. |
| 5,654,183 A | 8/1997 | Anderson et al. |
| 5,691,203 A | 11/1997 | Katsuen et al. |
| 5,695,997 A | 12/1997 | Ruoslahti et al. |
| 5,750,376 A | 5/1998 | Weiss et al. |
| 5,753,506 A | 5/1998 | Johe |
| 5,766,948 A | 6/1998 | Gage et al. |
| 5,830,621 A | 11/1998 | Suzuki et al. |
| 5,830,651 A | 11/1998 | Cauley et al. |
| 5,849,553 A | 12/1998 | Anderson et al. |
| 5,851,832 A | 12/1998 | Weiss et al. |
| 5,916,875 A | 6/1999 | Ruoslahti et al. |
| 5,928,947 A | 7/1999 | Anderson et al. |
| 5,942,435 A | 8/1999 | Wheeler |
| 5,968,829 A | 10/1999 | Carpenter |
| 6,040,180 A | 3/2000 | Johe |
| 6,046,289 A | 4/2000 | Komazawa et al. |
| 6,090,622 A | 7/2000 | Gearhart et al. |
| 6,121,027 A | 9/2000 | Clapper et al. |
| 6,200,806 B1 | 3/2001 | Thomson |
| 6,235,537 B1 | 5/2001 | North et al. |
| 6,238,922 B1 | 5/2001 | Uchida |
| 6,245,564 B1 | 6/2001 | Goldman et al. |
| 6,306,922 B1 | 10/2001 | Hubbell et al. |
| 6,316,522 B1 | 11/2001 | Loomis et al. |
| 6,514,734 B1 | 2/2003 | Clapper et al. |
| 6,534,130 B1 | 3/2003 | Maag et al. |
| 6,610,826 B1 | 8/2003 | Meyer et al. |
| 6,887,706 B2 | 5/2005 | Zhang et al. |
| 6,897,271 B1 | 5/2005 | Domschke et al. |

(Continued)

FOREIGN PATENT DOCUMENTS

| | | |
|---|---|---|
| CA | 2253078 | 5/2001 |
| EP | 0373626 | 6/1990 |

(Continued)

OTHER PUBLICATIONS

"Neural Stem Cell—The Seed Cell of the Neural System," China J. Orthop. Trauma 2(4), Dec. 2000, pp. 329-331.
Ahmed, Hydrogels: Preparation, characterization, and applications, 2013 J. Adv. Res., published online Jul. 18, 2013, available at http://dx.doi.org/10.1016/j.jare.2013.07.006.
Akiyama, Y. et al., "Remyelination of the rat spinal cord by transplantation of identified bone marrow stromal cells", J. Neurosci. 22(15), 2002, pp. 6623-6630.
Amit, M. et al., "Feeder-free culture of human embryonic stem cells", Meth. Enzymol. 420, 2006, pp. 37-49.

(Continued)

*Primary Examiner* — Thaian N Ton
(74) *Attorney, Agent, or Firm* — Krista P. Kauppinen

(57) ABSTRACT

Synthetic surfaces suitable for culturing stem cell derived oligodendrocyte progenitor cells contain acrylate polymers formed from one or more acrylate monomers. The acrylate surfaces, in many cases, are suitable for culturing stem cell derived oligodendrocyte progenitor cells in chemically defined media.

8 Claims, 10 Drawing Sheets

(56) References Cited

U.S. PATENT DOCUMENTS

| | | |
|---|---|---|
| 7,067,194 B2 | 6/2006 | Mao et al. |
| 7,285,415 B2 | 10/2007 | Keirstead et al. |
| 7,384,984 B2 | 6/2008 | Lewandowski et al. |
| 7,402,339 B2 | 7/2008 | Schmidt et al. |
| 7,615,593 B2 | 11/2009 | Kao et al. |
| 8,168,433 B2 | 5/2012 | Gehman et al. |
| 8,298,606 B2 | 10/2012 | Healy et al. |
| 8,513,009 B2 | 8/2013 | Shogbon et al. |
| 9,238,794 B2 * | 1/2016 | Shogbon ............ C12N 5/0068 |
| 2001/0039316 A1 | 11/2001 | Campbell et al. |
| 2002/0019046 A1 | 2/2002 | Carpenter et al. |
| 2003/0029418 A1 | 2/2003 | Deschamps et al. |
| 2003/0083389 A1 | 5/2003 | Kao et al. |
| 2003/0180268 A1 | 9/2003 | Atala |
| 2003/0215946 A1 | 11/2003 | Nair et al. |
| 2004/0096505 A1 | 5/2004 | Woerly |
| 2004/0197557 A1 | 10/2004 | Eshraghi et al. |
| 2005/0019747 A1 | 1/2005 | Anderson et al. |
| 2005/0036980 A1 | 2/2005 | Chaney et al. |
| 2005/0059150 A1 | 3/2005 | Guarino et al. |
| 2005/0136536 A1 | 6/2005 | Anderson et al. |
| 2005/0265980 A1 | 12/2005 | Chen et al. |
| 2005/0276858 A1 | 12/2005 | Kao et al. |
| 2005/0281857 A1 | 12/2005 | Heyer et al. |
| 2006/0100369 A1 | 5/2006 | Kao et al. |
| 2006/0127878 A1 | 6/2006 | Salomon et al. |
| 2006/0134050 A1 | 6/2006 | Griffith et al. |
| 2006/0172415 A1 | 8/2006 | Okazaki |
| 2006/0228386 A1 | 10/2006 | Stephens et al. |
| 2006/0263878 A1 | 11/2006 | Mochitate |
| 2007/0026518 A1 | 2/2007 | Healy et al. |
| 2007/0029924 A1 | 2/2007 | Ushifusa et al. |
| 2007/0082393 A1 | 4/2007 | Lodhi et al. |
| 2007/0167354 A1 | 7/2007 | Kennedy et al. |
| 2007/0254378 A1 | 11/2007 | Zhang et al. |
| 2007/0269886 A1 | 11/2007 | Qian et al. |
| 2008/0017827 A1 | 1/2008 | Ito et al. |
| 2008/0213389 A1 | 9/2008 | Lelkes et al. |
| 2009/0043079 A1 | 2/2009 | Chen et al. |
| 2009/0081797 A1 | 3/2009 | Fadeev et al. |
| 2009/0110907 A1 | 4/2009 | Jiang et al. |
| 2009/0191626 A1 | 7/2009 | Shogbon et al. |
| 2009/0191627 A1 | 7/2009 | Fadeev et al. |
| 2009/0191632 A1 | 7/2009 | Fadeev et al. |
| 2009/0191633 A1 | 7/2009 | Shogbon et al. |
| 2009/0203065 A1 | 8/2009 | Gehman et al. |
| 2010/0099160 A1 | 4/2010 | Jiang et al. |
| 2010/0304482 A1 | 12/2010 | Deshayes et al. |

FOREIGN PATENT DOCUMENTS

| | | |
|---|---|---|
| EP | 0450254 | 10/1991 |
| EP | 0614923 | 1/2000 |
| JP | 58-146280 | 8/1983 |
| JP | 59-093733 | 5/1984 |
| JP | 2001-309682 | 12/1989 |
| JP | 5-271579 | 10/1993 |
| JP | 2002-191353 | 7/2002 |
| JP | 2004-129561 | 4/2004 |
| JP | 2006-042794 | 2/2006 |
| JP | 2006-174826 | 7/2006 |
| WO | 1988/008448 | 11/1988 |
| WO | 1997/007200 | 2/1997 |
| WO | 1997/032608 | 9/1997 |
| WO | 1998/031734 | 7/1998 |
| WO | 1998/050526 | 11/1998 |
| WO | 1999/001159 | 1/1999 |
| WO | 1999/020741 | 4/1999 |
| WO | 1999/031126 | 6/1999 |
| WO | 2000/023571 | 4/2000 |
| WO | 2001/028342 | 4/2001 |
| WO | 2001/051610 | 7/2001 |
| WO | 2001/068815 | 9/2001 |
| WO | 2001/088104 | 11/2001 |
| WO | 2001/098463 | 12/2001 |
| WO | 2002/006373 | 1/2002 |
| WO | 2002/062961 | 8/2002 |
| WO | 2002/062969 | 8/2002 |
| WO | 2003/000868 | 1/2003 |
| WO | 2003/029418 | 4/2003 |
| WO | 2004/037164 | 5/2004 |
| WO | 2005/021634 | 3/2005 |
| WO | 2005/028619 | 3/2005 |
| WO | 2005/040191 | 5/2005 |
| WO | 2005/053621 | 6/2005 |
| WO | 2006/105278 | 10/2006 |
| WO | 2007/012144 | 2/2007 |
| WO | 2007/104107 | 9/2007 |
| WO | 2008/083390 | 7/2008 |
| WO | 2008/109117 | 9/2008 |
| WO | 2008/118392 | 10/2008 |
| WO | 2009/032117 | 3/2009 |
| WO | 2009/099555 | 8/2009 |

OTHER PUBLICATIONS

Anderson, D. et al., "Nanoliter-scale synthesis of arrayed biomaterials and application to human embryonic stem cells", Nature Biotech. 22(7), 2004, 863-6.

Arsenijevic, Y. et al., "Isolation of multipotent neural precursors residing in the cortex of the adult human brain", Exp. Neurol. 170(1), 2001, pp. 48-62.

Bain, G. et al., "Embryonic Stem Cells Express Neuronal Properties in Vitro", Dev. Biol. 168:342-57 (1995).

Bain, G. et al., "Expression of Retinoid X Receptors in P19 Embryonal Carcinoma Cells and Embryonic Stem Cells", Biochem. Biophys. Res. Comm. 200(3):1252-1256 (1994).

Bain, G. et al., "From embryonal carcinoma cells to neurons: the p19 pathway", BioEssays 16(5):343-348 (1994).

Bain, G. et al., "Neural Cells Derived by In Vitro Differentiation of P19 and Embryonic Stem Cells", Perspect. Dev. Neurobiol. 5:175-178 (1998).

Barber, T. et al., "Ligand density characterization of peptide-modified biomaterials," Biomaterials 26, 2005, 6897-905.

Barber, T. et al., "Peptide-modified p(AAm-co-Eg/AAc) IPNs grafted to bulk titanium modulate osteoblast behavior in vitro," J. Biomed. Mater. Res. 64A 2002, 38-47.

Barres, B. et al., "A novel role for thyroid hormone, glucocorticoids and retinoic acid in timing oligodendrocyte development", Development 120(5), 1994, pp. 1097-1108.

Barres, B. et al., "Cell death and control of cell survival in the oligodendrocyte lineage", Cell 70(1), 1992, pp. 31-46.

Bearinger, J. et al., "Biomolecular modification of p(AAm-co-EG/AA) IPNs supports osteoblast adhesion and phenotypic expression," J. Biomed. Sci. Polymer Edn. 9(7) 1998, 629-52.

Bearinger, J. et al., "P(AAm-co-EG) interpenetrating polymer networks grafted tooxide surfaces: surface characterization, protein adsorption, and cell detachment studies," Langmuir 13(19) 1997, 5175-83.

Besse, D. et al., "Synthesis of selenocysteine peptides and their oxidation to diselenide-bridged compounds", J. Pept. Sci. 3(6):442-453 (1997).

Billon, N. et al., "Normal timing of oligodendrocyte development from genetically engineered, lineage-selectable mouse ES cells", J. Cell Sci. 115(18), 2002, pp. 3657-3665.

Bjorklund, L. et al., "Embryonic stem cells develop into functional dopaminergic neurons after transplantation in a Parkinson rat model", Proc. Natl. Acad. Sci. USA 99(4), 2002, pp. 2344-2349.

Blakemore, W. et al., "The origin of remyelinating cells in the central nervous system", J. Neuroimmunol. 98(1):69-76 (1999).

Bottenstein, J., "Growth requirements in vitro of oligodendrocyte cell lines and neonatal rat brain oligodendrocytes", Proc. Natl. Acad. Sci. USA 83(6), 1986, pp. 1955-1959.

Braam, S. et al., "Recombinant vitronectin is a functionally defined substrate that supports human embryonic stem cell self renewal via AVB5 integrin," Stem Cells 26(9)2008, 2257-65.

(56) References Cited

OTHER PUBLICATIONS

Brandley, B. et al., "Covalent attachment of an Arg-Gly-Asp sequence peptide to derivatizable polyacrylamide surfaces: sequence peptide to derivatizable polyacrylamide surfaces: support of fibroblast adhesion and long-term growth", Anal. Biochem. 172, 1988, pp. 270-278.
Brustle, O et al., "In vitro generated neural precursors participate in mammalian brain development", Proc. Natl. Acad. Sci. USA 94, 1997, pp. 14809-14814.
Brustle, O. et al., "Embryonic Stem Cell-Derived Glial Precursors: A Source of Myelinating Transplants", Science 285, 1999, pp. 754-756.
Carpenter, M. et al., "Enrichment of neurons and neural precursors from human embryonic stem cells", Exp. Neurol. 172(2), 2001, 383-397.
Chandross, K. et al., "Tracking oligodendrocytes during development and regeneration", Microsc. Res. Tech. 52(6):766-777 (2001).
Chen, H. et al., "Gene transfer and expression in oligodendrocytes under the control of myelin basic protein transcriptional control region mediated by adeno-associated virus", Gene Ther. 5(1), 1998, pp. 50-58.
Chen, Y. et al., "Improvement in the primary cultures of neonatal rat cardiac myocytes", Chinese J. Biologicals 19(5), 2006, pp. 520-521.
Cowan, C. et al., "Derivation of embryonic stem-cell lines from human blastocysts", N. Engl. J. Med. 350(13), 2004, 1353-6.
Cruise, G. et al., "Characterization of permeability and network structure of interfacially photopolymerized poly(ethylene glycol) diacrylate hydrogels," Biomaterials 19, 1998, 1287-94.
Dawson, E. et al., "Biomaterials for stem cell differentiation," Adv. Drug Delivery Rev.60, 2008, 215-28.
Derda, R. et al., "Defined substrates for human embryonic stem cell growth identified from surface arrays", ACS Chem. Biol. 2(5), 2007, pp. 347-355.
Drumheller, P. et al., "Bioactive Peptides and Surface Design", Interfacial Phenomena and Bioproducts, J.L. Brash et al., Marcel Dekker, Inc., 1996, pp. 273-310.
Drumheller, P. et al., "Multifunctional poly(ethylene glycol) semi-interpenetrating polymer networks as highly selective adhesive substrates for bioadhesive peptide grafting", Biotechnol. Bioeng. 43, 1994, pp. 772-780.
Drumheller, P. et al., "Polymer networks with grafted cell adhesion peptides for highly biospecific cell adhesive substrates", Anal. Biochem. 222, 1994, pp. 380-388.
Drumheller, P. et al., "Surface immobilization of adhesion ligands for investigations of cell-substrate interactions", The Biomedical Engineering Handbook, J.D. Bronzino, Ed., CRC & IEEE Press, 2000, pp. 1583-1596.
Eccleston, P. et al., "The differentiation of oligodendrocytes in a serum-free hormone-supplemented medium", Brain Res. 318(1), 1984, pp. 1-9.
Fassler, R. et al., "Lack of beta-1 integrin gene in embryonic stem cells affects morphology, adhesion, and migration but not integration into the inner cell mass of blastocysts", J. Cell Biol. 128(5), 1995, pp. 979-988.
Fittkau, M. et al., "The selective modulation of endothelial cell mobility on RGD peptide containing surfaces by YIGSR peptides," Biomaterials 26 2005, 167-74.
Harbers, G. et al., "Development and characterization of a high-throughput system for assessing cell-surface receptor-ligand engagement," Langmuir 21(18), 2005, 8374-84.
Harbers, G. et al., "The effect of ligand type and density on osteoblast adhesion, proliferation and matrix mineralization," J. Biomed. Mater. Res. 75A, 2005, 855-69.
Hayes, B. et al., "Derivation, characterization, and in vitro differentiation of canine embryonic stem cells", Stem Cells 26, 2008, pp. 465-473.
Healy, K. et al., "Designing biomaterials to direct biological responses," Ann. NY Acad. Sci. 875, 1999, 24-35.
Healy, K. et al., "Molecular engineering of materials for bioreactivity," Curr. Op. Solid State Mater. Sci. 4, 1999, 381-7.

Heggli, M. et al., "Michael-type addition as a tool for surface functionalization," Bioconj. Chem. 14, 2003, 967-73.
Hern, D. et al., "Incorporation of adhesion peptides into nonadhesive hydrogels useful for tissue resurfacing," J. Biomed. Mater. Res. 39, 1998, 266-76.
Hersel, U. et al., "RGD modified polymers: biomaterials for stimulated cell adhesion and beyond", Biomaterials 24(24), 2003, pp. 4385-4415.
Fraichard, A. et al., "In Vitro Differentiation of Embryonic Stem Cells into Glial Cells and Functional Neurons", J. Cell Sci. 108, 1995, pp. 3181-3188.
Freed, C., "Will embryonic stem cells be a useful source of dopamine neurons for transplant into patients with Parkinson's disease?", Proc. Natl. Acad. Sci. USA 99, 2002, pp. 1755-1757.
Gehlsen, K. et al., "Inhibition of in vitro tumor cell invasion by Arg-Gly-Asp-containing synthetic peptides", J. Cell. Biol. 106(3), erratum in J Cell Biol Jun. 1989;108(6):following 2546, 1988, pp. 925-930.
Gottlieb, D., "An in vitro pathway from embryonic stem cells to neurons and glia", Cells Tissues Organs 165(3-4), 1999, pp. 165-172.
Gu, J. et al., "Selenium is required for normal upregulation of myelin genes in differentiating oligodendrocytes", J. Neurosci. Res. 47(6), 1997, pp. 626-635.
Guan, K. et al., "Embryonic stem cell-derived neurogenesis. Retinoic acid induction and lineage selection of neuronal cells", Cell Tissue Res. 305(2), 2001, pp. 171-176.
Hajihosseini, M., "Origin of oligodendrocytes within the human spinal cord", J. Neurosci. 16(24), 1996, pp. 7981-7994.
Hao, Y. et al., "The primary cultures of neonatal rat cardiac myocytes", Chinese Heart J. 13(6), Abstract in English, 2001, pp. 473-475.
Irwin, E. et al., "Analysis of interpenetrating polymer networks via quartz crystal microbalance with dissipation monitoring," Langmuir 21(12), 2005, 5529-36.
Itskovitz-Eldor, J. et al., "Differentiation of human embryonic stem cells into embryoid bodies comprising the three embryonic germ layers", Mol. Med. 6(2), 2000, 88-95.
Kalman, B. et al., "Spectrum and classification of inflammatory demyelinating diseases of the central nervous system", Curr. Neurol. Neurosci. Rep. 1(3), 2001, pp. 249-256.
Kamarun, D. et al., "A peptide cross-linked polyacrylamide hydrogel for the detection of human neutrophil elastase", Electrochimica Acta 54(22), 2009, pp. 4985-4990.
Kantlehner, M. et al., "Surface coating with cyclic RGD peptides stimulates osteoblast adhesion and proliferation as well as bone formation", Chembiochem. 1(2), 2000, pp. 107-114.
Keirstead, H. et al., "A quantifiable model of axonal regeneration in the demyelinated adult rat spinal cord", Exp. Neurol. 151(2), 1998, pp. 303-313.
Keirstead, H., "Enhanced axonal regeneration following combined demyelination plus schwann cell transplantation therapy in the injured adult spinal cord", Exp. Neurol. 159(1), 1999, pp. 225-236.
Keirstead, H. et al., "Identification of post-mitotic oligodendrocytes incapable of remyelination within the demyelinated adult spinal cord", J. Neuropathol. Exp. Neurol. 56(11), 1997, pp. 1191-1201.
Hinks, G., "Depletion of endogenous oligodendrocyte progenitors rather than increased availability of survival factors is a likely explanation for enhanced survival of transplanted oligodendrocyte progenitors in X-irradiated compared to normal CNS", Neuropathol. Appl. Neurobiol. 27(1), 2001, pp. 59-67.
Ho, S. et al., "Arg-Gly-Asp peptides in polyurethanes: Design, synthesis, and characterization", Adv. Materials 6(2), 1994, pp. 130-132.
Holland, E., "Gliomagenesis: genetic alterations and mouse models", Nat. Rev. Genet. 2(2), 2001, pp. 120-129.
Holtkamp, M. et al., "Chronic inflammatory demyelinating polyradiculoneuropathy with histologically proven optic neuritis", Acta Neuropathol. 101(5), 2001, pp. 529-531.
Horak, D. et al., "Poly(2-hydroxyethyl methacrylate)-based slabs as a mouse embryonic stem cell support", Biomaterials 25(22), 2004, pp. 5249-5260.

(56) References Cited

OTHER PUBLICATIONS

Hubbell, J., "Biomaterials in tissue engineering," Biotechnol. 13, 1995, 565-76.
Hubbell, J. et al., "Surface-grafted cell-binding peptides in tissue engineering of the vascular graft," Ann. NY Acad. Sci. 665, 1992, 253-8.
Huebsch, N. et al., "Analysis of sterilization protocols for peptide-modified hydrogels,"J. Biomed. Mater. Res. 74B(1), 2005, 440-7.
Koide, T. et al., "Syntheses and biological activities of selenium analogs of alpha-rat atrial natriuretic peptide", Chem. Pharm. Bull. 41(9), 1993, pp. 1596-1600.
Koide, T. et al., "Synthetic study on selenocystine-containing peptides", Chem. Pharm. Bull. 41(3), 1993, pp. 502-506.
Kolhar, P. et al., "Synthetic surfaces for human embryonic stem cell adhesion, proliferation and culture", AIChE Conference Abstract, http://aiche.contex.com/aiche/2009/webprogrampreliminary/Paper165220.htm, 2009, p. 1.
Kornblum, H. et al., "Molecular markers in CNS stem cell research: hitting a moving target", Nature Rev. Neurosci. 2(11), 2001, pp. 843-846.
Kou, J. et al., "pH-dependent swelling and solute diffusion characteristics of poly(hydroxyethyl methacrylate-co-methacrylic acid) hydrogels", Pharm. Res. 5(9), 1988, pp. 592-597.
Kroupova, J. et al., "Functional polymer hydrogels for embryonic stem cell support", J. Biomed. Mat. Res. 76B(2), 2005, pp. 315-325.
Kuo, H. et al., "Differentiation of monkey embryonic stem cells into neural lineages", Biol. Reprod. 68(5), 2002, pp. 1727-1735.
Laflamme, M. et al., "Cardiomyocytes derived from human embryonic stem cells in pro-survival factors enhance function of infarcted rat hearts", Nature Biotechnol. 25, 2007, 1015-24.
Keirstead, H. et al., "In vivo immunological suppression of spinal cord myelin development", Brain Res. Bull. 44(6), 1997, pp. 727-734.
Keirstead, H. et al., "Polysialylated neural cell adhesion molecule-positive CNS precursors generate both oligodendrocytes and Schwann cells to remyelinate the CNS after transplantation", J. Neurosci. 19(17), 1999, pp. 7529-7536.
Keirstead, H. et al., "Response of the oligodendrocyte progenitor cell population (defined by NG2 labelling) to demyelination of the adult spinal cord", Glia 22(2), 1998, pp. 161-170.
Keirstead, H., "Stem cell transplantation into the central nervous system and the control of differentiation", J. Neurosci. Res. 63(3), 2001, pp. 233-236.
Keirstead, H. et al., "The role of oligodendrocytes and oligodendrocyte progenitors in CNS remyelination", Adv. Exp. Med. Biol. 468, 1999, pp. 183-197.
Kim, S.-Y. et al., "Synthesis and characterization of injectable poly) N-isopropylacrylamide-co-acrylic acid) hydrogels with proteolytically degradable cross-links," Biomacromolecules 4, 2003, 1214-23.
Kim, S.-Y. et al., "Synthetic MMP-13 degradable ECMs based on poly(N-isopropyl acrylamide-co-acrylic acid) semi interpenetrating polymer networks L degradation and cell migration," J. Biomed. Mater. Res. 75A(1), 2005, 73-88.
Klimanskaya, I. et al., "Human embryonic stem cells derived without feeder cells", Lancet 365(9471), 2005, 1636-41.
Ludwig, T. et al., "Derivation of human embryonic stem cells in defined conditions,"Nat. Biotechnol. 24(2), 2006, 185-7.
Lutolf, M. et al., "Synthesis and physicochemical characterization of end-linked poly (ethylene glycol)-co-peptide hydrogels formed by Michael-type addition," Biomacromolecules 4, 2003, 713-22.
Lutolf, M. et al., "Synthetic biomaterials as instructive extracellular microenvironments for morphogenesis in tissue engineering," Nature Biotechnol. 23, 2005, 47-55.
Mallon et al., Toward xeno-free culture of human embryonic stem cells, The International Journal of Biochemistry and Cell Biology, 38(7): 1063-1075, 2006.

Massia, S. et al., "An RGD spacing of 440nm is sufficient for integrin alpha V beta 3-mediated fibroblast spreading and 140nm for focal contact and stress fiber formation," J. Cell Biol. 114, 1991, 1089-100.
Massia, S. et al., "Covalently immobilized laminin peptide Tyr-Ile-Gly-Ser-Arg (YIGSR) supports cell spreading and co-localization of the 67-kilodalton laminin receptor with alpha-actinin and vinculin," J. Biol. Chem. 268, 1993, 8053-9.
Massia, S. et al., "Human endothelial cell interactions with surface-coupled adhesion peptides on a nonadhesive glass substrate and two polymeric biomaterials," J. Biomed. Mater. Res. 25, 1991, 223-42.
Massia, S. et al., "Immobilized amines and basic amino acids as mimetic heparin-binding domains for cell surface proteoglycan-mediated adhesion," J. Biol. Chem. 267,1992, 10133-41.
Lee, S-H. et al., "Efficient Generation of Midbrain and Hindbrain Neurons from Mouse Embryonic Stem Cells", Nat. Biotech. 18, 2000, pp. 675-679.
Li, M., "Generation of purified neural precursors from embryonic stem cells by lineage selection", Curr. Biol. 8, 1998, pp. 971-974.
Li, Y. et al., "Expansion of human embryonic stem cells in defined serum-free medium devoid of animal-derived products," Biotechnol. Bioeng. 91(6), 2005, 688-98.
Li, Y-J. et al., "Hydrogels as artificial matrices for human embryonic stem cell self-renewal," J. Biomed. Mater. Res. Part A 79(1) 2006, 1-5.
Lie, D. et al., "The adult substantia nigra contains progenitor cells with neurogenic potential", J. Neurosci. 22(15), 2002, pp. 6639-6649.
Liu, S. et al., "Embryonic Stem Cells Differentiate into Oligodendrocytes and Myelinate in Culture and After Spinal Cord Transplantation", Proc. Natl. Acad. Sci. USA 97, 2000, pp. 6126-6131.
Liu, X. et al., "Micelles and hollow nanospheres based on epsilon-caprolactone-containing polymers in aqueous media", Angewandte Chemie 114(16), 2002, pp. 3074-3077.
Lu, J. et al., "Defined culture conditions of human embryonic stem cells," Proc. Natl. Acad. Sci. USA 103(15), 2006, 5688-93.
Nih, "Stem Cells: Scientific Progress and Future Research Directions", Dept. Health & Human Svcs. Chapter 1, 2001, pp. 1-4.
Nishiyama, A. et al., "Co-localization of NG2 proteoglycan and PDGF alpha-receptor on O2A progenitor cells in the developing rat brain", J. Neurosci. Res. 43(3), 1996, pp. 299-314.
Nistor, G. et al., "Human embryonic stem cells differentiate into oligodendrocytes in high purity and myelinate after spinal cord transplantation", Glia 49, 2005, pp. 385-396.
Nistor, G. et al., "Induction of high purity oligodendrocyte cultures from human embryonic stem cells", 32nd Annual Meeting of the Society for Neuroscience, Orlando, FL, Nov. 2-7, 2002, Abstract No. 726.16.
O'Shea, K., "Neuronal differentiation of mouse embryonic stem cells: lineage selection and forced differentiation paradigms", Blood Cells Mol. Dis. 27(3), 2001, pp. 705-712.
Ostenfeld, T. et al., "Regional specification of rodent and human neurospheres", Dev. Brain Res. 134(1-2), 2002, pp. 43-55.
Pardo, B. et al., "Differentiation of rat striatal embryonic stem cells in vitro: monolayer culture vs. three-dimensional coculture with differentiated brain cells", J. Neurosci. Res. 59(4), 2000, pp. 504-512.
Park, K. et al., "Transplantation of neural progenitor and stem cells: developmental insights may suggest new therapies for spinal cord and other CNS dysfunction", J. Neurotrauma 16(8), 1999, pp. 675-687.
Massia, S. et al., "Vascular endothelial cell adhesion and spreading promoted by the peptide REDV of the IIICS region of plasma fibronectin is mediated by integrin alpha 4 beta 1," J. Biol. Chem. 267, 1992, 14019-26.
McDonald, J., "Repairing the damaged spinal cord", Sci. Am. 281(3), 1999, pp. 64-73.
McDonald, J. et al., "Transplanted Embryonic Stem Cells Survive, Differentiate and Promote Recovery in Injured Rat Spinal Cord", Nature Med. 5, 1999, pp. 1410-1412.

(56) References Cited

OTHER PUBLICATIONS

Melkoumian, Z. et al., "Synthetic peptide-acrylate surfaces for long-term self-renewal and cardiomyocyte differentiation of human embryonic stem cells", Nature Biotechnol. 28(6), 2010, pp. 606-610.
Model, M. et al., "Quantification of the surface density of a fluorescent label with the optical microscope," J. Biomed. Mater. Res. 50, 2000, 90-6.
Mujtaba, T. et al., "Lineage-restricted neural precursors can be isolated from both the mouse neural tube and cultured ES cells", Dev. Biol. 214, 1999, pp. 113-127.
Murray, K. et al., "Emergence of oligodendrocytes from human neural spheres", J. Neurosci. Res. 50, 1990, pp. 146-156.
Nguyen, Photopolymerizable hydrogels for tissue engineering applications, Biomaterials 23: 4307-4314, 2002.
Rezania, A. et al., "Biomolecular surface engineering of materials for controlling bonecell adhesion and spreading," Mater. Res. Soc. Symp. Proc. 530, 1998, 99-103.
Rezania, A. et al., "Integrin subunits responsible for adhesion of human osteoblast-like cells to biomimetic peptide surfaces," J. Ortho. Res. 17(4), 1999, 615-23.
Rezania, A. et al., "The detachment strength and morphology of bone cells contacting materials modified with a peptide sequence found within bone sialoprotein," J. Biomed. Mater. Res. 37(1), 1997, 9-19.
Rezania, A. et al., "The effect of peptide surface density on mineralization of a matrix deposited by osteogenic cells," J. Biomed. Mater. Res. 52, 2000, 595-600.
Rifkin, D. et al., "Bone matrix to growth factors: location, location, location", J. Cell. Biol. 190(6), 2010, pp. 949-951.
Roy, N. et al., "Identification, isolation, and promoter-defined separation of mitotic oligodendrocyte progenitor cells from the adult human subcortical white matter", J. Neurosci. 19, 1999, pp. 9986-9995.
Ruffini, F. et al., "Distinctive properties of human adult brain-derived myelin progenitor cells", Am. J. Pathol. 165, 2004, pp. 2167-2175.
Saha, K. et al., "Biomimetic interfacial interpenetration polymer networks control neural stem cell behavior," J. Biomed. Mater. Res. 81A(1), 2007, 240-9.
Park, S. et al., "Surface modification of poly(ethylene terephthalate) angioplasty balloons with a hydrophilic poly(acrylamide-co-ethylene glycol) interpenetrating network coating," J. Biomed. Mater. Res. 53(5), 2000, 568-76.
Park, S. et al., "Nanoparticulate DNA packaging using terpolymers of poly(lysine-g-lactide-b-ethylene glycol)," Bioconjugate Chem. 14(2), 2003, 311-9.
Pratt, A. et al., "Synthetic extracellular matrices for in situ tissue engineering," Biotechnol. Bioeng. 86(1), 2004, 27-36.
Reubinoff, B. et al., "Embryonic stem cells lines from human blastocysts: somatic differentiation in vitro", Nature Biotechnol. 18, 2000, pp. 399-404.
Reubinoff, B. et al., "Neural progenitors from human embryonic stem cells", Nat. Biotech. 19, 2001, pp. 1134-1140.
Rezania, A. et al., "A probabilistic approach to measure the strength of bone cell adhesion to chemically modified surfaces," Ann. Biomed. Eng. 25, 1997, 190-203.
Rezania, A. et al., "Bioactivation of metal oxide surfaces: I. Surface characterizationand cell response," Langmuir 15, 1999, 6931-9.
Rezania, A. et al., "Biomimetic peptide surfaces that regulate adhesion, spreading, cytoskeletal organization and mineralization of the matrix deposited byosteoblast-like cells," Biotechnol. Progress 15(1), 1999, 19-32.
Stile, R. et al., "Poly(N-isopropylacrylamide)-based semi-interpenetrating polymer networks for tissue engineering application effects of linear poly(acrylic acid) chains on phase behavior," Biomacromolecules 3, 2002, 591-600.
Stile, R. et al., "Poly(N-isopropylacrylamide)-based semi-interpenetrating polymer networks for tissue engineering applications. Effects of linear poly(acrylic acid) chains on rheology," J. Biomater. Sci. Polym. Ed. 15(7), 2004, 865-78.
Stile, R. et al., "Synthesis and characterization of injectable poly (N-isopropylacrylamide)-based hydrogels that support tissue formation in vitro," Macromolecules 32, 1999, 7370-7379.
Stile, R. et al., "Thermo-responsive peptide-modified hydrogels for tissue regeneration," Biomacromolecules 2, 2001, 185-94.
Stojkovic, P. et al., "Human-serum matrix supports undifferentiated growth of human embryonic stem cells," Stem Cells 23(7), 2005, 895-902.
Svendsen, C. et al., "A new method for the rapid and long term growth of human neural precursor cells", J. Neurosci. Meth. 85, 1998, pp. 141-152.
Takahashi, K. et al., "Induction of pluripotent stem cells from adult human fibroblasts by defined factors", Cell 131(5), 2007, 861-72.
Tanahashi, K. et al., "Protein adsorption and smooth muscle cell adhesion on biodegradable agmatine-modified poly(propylene fumarate-co-ethylene glycol) hydrogels", J. Biomed. Mat. Res. 67(2), 2003, pp. 448-457.
Scolding, N. et al., "Identification of A2B5-positive putative oligodendrocyte progenitor cells and A2B5-positive astrocytes in adult human white matter", Neurosci. 89(1), 1999, pp. 1-4.
Scolding, N. , "Oligodendrocyte progenitors are present in the normal adult human CNS and in the lesions of multiple sclerosis", Brain 121(12), 1998, pp. 2219-2220.
Shin, H. et al., "Attachment, proliferation, and migration of marrow stromal osteoblasts cultured on biomimetic hydrogels modified with an osteopontin-derived peptide", Biomaterials 25(5), 2004, pp. 895-906.
Singh, A. et al., "Chibby, an antagonist of the Wnt/Beta-catenin pathway, facilitates cardiomyocyte differentiation of murine embryonic stem cells", Circulation 115, 2007, pp. 617-626.
Skottman, H. et al., "Culture conditions for human embryonic stem cells," Reprod. 132(5), 2006, 691-8.
Song, J. et al., "Mineralization of synthetic polymer scaffolds: a bottom-up approach for the development of artificial bone", J. Am. Chem. Soc. 127(10), 2005, pp. 3366-3372.
Stallcup, W. et al., "Bipotential glial precursor cells of the optic nerve express the NG2 proteoglycan", J. Neurosci. 7, 1987, pp. 2737-2744.
Stile, R. et al., "Axisymmetric adhesion test to examine the interfacial interactions between biologically-modified networks and models of the extracellular matrix," Langmuir 19, 2003, 1853-60.
Xu, C. et al., "Cardiac Bodies: A novel culture method for enrichment of cardiomyocytes derived from human embryonic stem cells", Stem Cells & Dev. 15, 2006, 631-9.
Xu, C. et al., "Feeder-free growth of undifferentiated human embryonic stem cells", Nature Biotech. 19, 2001, 971-4.
Xu, C. et al., "Human embryonic stem cell-derived cardiomyocytes can be maintained in defined medium without serum", Stem Cells Dev. 15, 2006, pp. 931-941.
Xu, X. et al., "Activin, BMP and FGF pathways cooperate to promote endoderm and pancreatic lineage cell differentiation from human embryonic stem cells", Mech. Dev. 128, 2011, pp. 412-427.
Yu, J. et al., "Induced pluripotent stem cell lines derived from human somatic cells", Science 318, 2007, 1917-20.
Zhang, S. et al., "Adult brain retains the potential to generate oligodendroglial progenitors with extensive myelination capacity", Proc. Natl. Acad. Sci. USA 96(7), 1999, pp. 4089-4094.
Zhang, S. et al., "Tracing human oligodendroglial development in vitro", J. Neurosci. Res. 59, 2000, pp. 421-429.
Zhang, S-C. et al., "In vitro differentiation of transplantable neural precursors from human embryonic stem cells", Nature Biotech. 19, 2001, pp. 1129-1133.
Thomas, C. et al., "Materials designed to control and examine the function of singlecells," Mater. Res. Soc. Symp. Proc. 530, 1998, 55-58.
Thomson, J. et al., "Embryonic stem cell lines derived from human blastocysts", Science 282, 1998, 1145-7.
Thomson, J. et al., "Neural Differentiation of Rhesus Embryonic Stem Cells", APMIS 106, 1998, pp. 149-156.
Ueda, S. et al., "Establishment of rat embryonic stem cells and making of chimera rats", PLoS ONE 3(7), 2009, pp. 1-9.

(56) References Cited

OTHER PUBLICATIONS

Whang, K. et al., "A biodegradable polymer scaffold for delivery of osteotropic factors," Biomaterials 21, 2000, 2545-51.
Wilson, H. et al., "Human oligodendrocyte precursor cells in vitro: phenotypic analysis and differential response to growth factors", Glia 44, 2003, pp. 153-165.
Wohl, C. et al., "Retinoic acid enhances neuronal proliferation and astroglial differentiation in cultures of CNS stem cell-derived precursors", J. Neurobiol. 37, 1998, pp. 281-290.
Xian, H. et al., "A subset of ES-cell-derived neural cells marked by gene targeting", Stem Cells 21(1), 2003, pp. 41-49.
Zhang et al., Oligodendrocyte Progenitor Cells Derived from Human Embryonic Stem Cells Express Neurotrophic Factors, Stem Cells & Development, 15: 943-952, 2006.
Zhu, J. et al., "Design and synthesis of biomimetic hydrogel scaffolds with controlled organization of cyclic RGD peptides", Bioconjug. Chem. 20(2), 2009, pp. 333-339.
Zhu, J. et al., "Extracellular Matrix-like Cell-Adhesive Hydrogels from RGD-Containing Poly(ethylene glycol) Diacrylate", Macromolecules 39(4), 2006, pp. 1305-1307.

\* cited by examiner 123-2

95-2

Matrigel 123-2

122-3

Matrigel

Matrigel 22-2

22-3

133-4

24-10

72-2

SYNTHETIC SURFACES FOR CULTURING STEM CELL DERIVED OLIGODENDROCYTE PROGENITOR CELLS

PRIORITY

This application is a continuation of U.S. application Ser. No. 14/997,999, filed Jan. 18, 2016 (now abandoned), which is a continuation of U.S. application Ser. No. 13/946,032, filed Jul. 19, 2013 (now U.S. Pat. No. 9,238,794), which is a continuation of U.S. application Ser. No. 12/362,250, filed Jan. 29, 2009 (now U.S. Pat. No. 8,513,009), which claims priority to U.S. Provisional Application No. 61/063,010, filed Jan. 30, 2008. All of the above priority applications are hereby incorporated by reference in their entireties.

FIELD

The present disclosure relates to cell culture articles and methods of use thereof, and more particularly to articles for supporting the culture of stem cell derived oligodendrocyte progenitor cells.

BACKGROUND

Pluripotent stem cells, such as human embryonic stem cells (hESCs) have the ability to differentiate into any of the three germ layers, giving rise to any adult cell type in the human body. This unique property provides a potential for developing new treatments for a number of serious cell degenerative diseases, such as diabetes, spinal cord injury, heart disease and the like. For example, spinal cord damage is generally irreversible with current treatments, leaving approximately 250,000 Americans in a devastating position. However, as stem cell research has developed, new exciting possibilities have arisen for people suffering from spinal cord injury. ES cell-derived neural cells have been used by researchers to treat nervous system disorders in animal models. In earlier work, researchers showed that mouse ES cells could be stimulated to differentiate into neural cells that, when transplanted into mice with neurological disorders, helped to restore normal function.

However there remain obstacles in the development of such hESC-based treatments. Such obstacles include obtaining and maintaining adequate numbers of undifferentiated hESCs in tissue culture and controlling their differentiation in order to produce specific cell types. Stem cell cultures, such as hESC cell cultures are typically seeded with a small number of cells from a cell bank or stock and then amplified in the undifferentiated state until differentiation is desired for a given therapeutic application To accomplish this, the hESC or their differentiated cells are currently cultured in the presence of surfaces or media containing animal-derived components, such as feeder layers, fetal bovine serum, or MATRIGEL®. These animal-derived additions to the culture environment expose the cells to potentially harmful viruses or other infectious agents which could be transferred to patients or compromise general culture and maintenance of the hESCs. In addition, such biological products are vulnerable to batch variation, immune response and limited shelf-life.

Some steps have been taken to culture hESCs either in media or on surfaces that are free of animal-derived components. However, the response of hESCs or their differentiated derivatives is difficult to predict as components of the surface or culture medium change. Yet some advances have been made. For example, hESC-derived oligodendrocyte progenitor cells (OPCs) have been cultured in defined serum-free medium. While such culture systems are not completely xeno-free culture systems when the matrices employed contain animal-derived components, such as gelatin and MATRIGEL, they do provide a step toward the eventual clinical application of hESC-derived OPCs. By way of further example, some synthetic surfaces have been identified that can support differentiation of human epithelial stem cells into epithelial cells. However, the systems employed relied on serum medium for the cell culture, which still potentially causes problem as described before for all biological animal derived components. To date, a completely animal free system employing a chemically defined medium and a synthetic surface has not yet been identified for culturing stem cells or cells derived from stem cells.

BRIEF SUMMARY

The present disclosure describes, inter alia, synthetic surfaces useful in the culture of stem cell-derived OPCs in chemically defined media.

In an embodiment, a method for culturing oligodendrocyte progenitor cells is provided. The method includes depositing a suspension containing the oligodendrocyte progenitor cells on a polymer material and culturing the deposited oligodendrocyte progenitor cells in a cell culture medium. The polymer material comprises a homopolymer or copolymer of selected one or more acrylate monomers.

In an embodiment, a culture of oligodendrocyte progenitor cells is provided. The culture includes an article having a polymer material disposed on a surface. The culture further includes the oligodendrocyte progenitor cells disposed on the polymer material and a culture medium in which the oligodendrocyte progenitor cells are cultured. The polymer material comprises a homopolymer or copolymer of selected one or more acrylate monomers.

In an embodiment, a cell culture article for culturing oligodendrocyte progenitor cells in a chemically defined medium is provided. The article includes a substrate having a surface and a polymer material disposed on the surface. The polymer material comprises a homopolymer or copolymer of selected one or more acrylate monomers.

One or more of the various embodiments presented herein provide one or more advantages over prior surfaces for culturing stem cell-derived OPCs. For example, the synthetic surfaces reduce potential contamination issues associated with surfaces having components obtained from or derived from animal sources. Such surfaces may also provide for improved shelf life compared to those surfaces with biological components. The ability to culture stem cell-derived OPCs in chemically-defined media further reduces potential contamination issues. In addition, there will likely be less batch to batch variation in the ability of the synthetic surfaces or chemically defined media, resulting in improved reproducibility of culture results and expectations. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

The present disclosure describes, inter alia, articles having synthetic surfaces for culturing stem cell-derived OPCs and methods for culturing stem cell-derived OPCs on such surfaces. In some embodiments, the synthetic surfaces are used in combination with a chemically defined medium to culture stem cell-derived OPCs. The surfaces may be useful in differentiating stem cells, such as hESCs, into OPCs or for proliferating such stem cell-derived OPCs.

1. Cell Culture Article

Figure 1A:
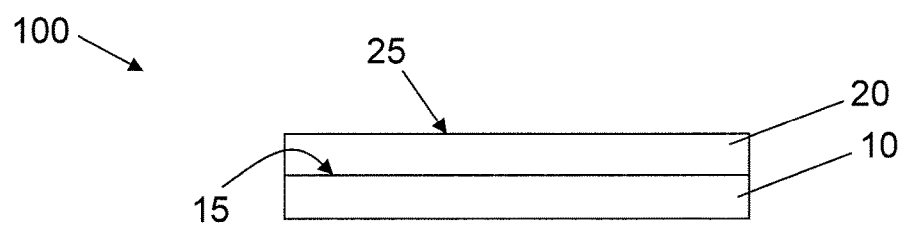
FIG. 1A and FIG. 1B are schematic diagrams of side views of synthetic polymer layer coated articles.

Referring to FIG. 1, a schematic diagram of article 100 for culturing cells is shown. The article 100 includes a base material substrate 10 having a surface 15. A synthetic polymer coating layer 20 is disposed on the surface 15 of the base material 10. While not shown, it will be understood that synthetic polymer coating 20 may be disposed on a portion of base material 10. The base material 10 may be any material suitable for culturing cells, including a ceramic substance, a glass, a plastic, a polymer or co-polymer, any combinations thereof, or a coating of one material on another. Such base materials 10 include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

Examples of articles 100 suitable for cell culture include single and multi-well plates, such as 6, 12, 96, 384, and 1536 well plates, jars, petri dishes, flasks, beakers, plates, roller bottles, slides, such as chambered and multichambered culture slides, tubes, cover slips, cups, spinner bottles, perfusion chambers, bioreactors, CellSTACKs® and fermenters.

Synthetic polymer coating 20 provides a surface 25 on which cells may be cultured. The synthetic polymer surface 20 includes polymerized acrylate monomers, selected from the group of monomers provided in Table 1 below. Other materials (not shown), such as peptides, may be incorporated into or conjugated to synthetic polymer surface to produce a biomimetic surface.

TABLE 1

List of acrylate monomers

| Monomer name | Monomer structure |
|---|---|
| Tetra(ethylene glycol) diacrylate | 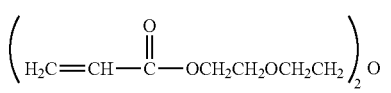 |
| Glycerol dimethacrylate |  |

TABLE 1-continued

List of acrylate monomers

| Monomer name | Monomer structure |
|---|---|
| Triethylene glycol dimethacrylate | $H_2C=C(CH_3)-C(=O)-(OCH_2CH_2)_3O-C(=O)-C(CH_3)=CH_2$ |
| 1,4-Butanediol dimethacrylate | $H_2C=C(CH_3)-C(=O)-OCH_2CH_2CH_2CH_2O-C(=O)-C(CH_3)=CH_2$ |
| Poly(ethylene glycol) diacrylate, $M_n \sim 258$ | $H_2C=CH-C(=O)-(OCH_2CH_2)_n-O-C(=O)-CH=CH_2$ |
| 1,6-Hexanediol diacrylate | $(H_2C=CH-C(=O)-OCH_2CH_2CH_2-)_2$ |
| 3-Hydroxy-2,2-dimethylpropyl 3-hydroxy-2,2-dimethylpropionate | $H_2C=CH-C(=O)-OCH_2-C(CH_3)_2-C(=O)-OCH_2-C(CH_3)_2-CH_2O-C(=O)-CH=CH_2$ |
| Neopentyl glycol propoxylate(1PO/OH) diacrylate | $H_2C=CH-C(=O)-O-(C_3H_6O)_mCH_2-C(CH_3)_2-CH_2(OC_3H_6)_nO-C(=O)-CH=CH_2$<br>$m + n \sim 2$ |
| Di(ethylene glycol) diacrylate | $H_2C=CH-C(=O)-OCH_2CH_2OCH_2CH_2O-C(=O)-CH=CH_2$ |
| Di(ethylene glycol) dimethacrylate | $H_2C=C(CH_3)-C(=O)-OCH_2CH_2OCH_2CH_2O-C(=O)-C(CH_3)=CH_2$ |
| Tetra(ethylene glycol) dimethacrylate | $H_2C=C(CH_3)-C(=O)-OCH_2CH_2OCH_2CH_2OCH_2CH_2OCH_2CH_2O-C(=O)-C(CH_3)=CH_2$ |
| 1,6-Hexanediol propoxylate diacrylate | $H_2C=CH-C(=O)-O-(C_3H_6O)_n-CH_2CH_2CH_2$<br>$H_2C=CH-C(=O)-O-(C_3H_6O)_n-CH_2CH_2CH_2$ |
| Glycerol 1,3-diglycerolate diacrylate | $H_2C=CH-C(=O)-OCH_2CH(OH)CH_2OCH_2CH(OH)CH_2OCH_2CH(OH)CH_2O-C(=O)-CH=CH_2$ |
| Neopentyl glycol diacrylate | $H_2C=CH-C(=O)-OCH_2-C(CH_3)_2-CH_2O-C(=O)-CH=CH_2$ |
| Neopentyl glycol dimethacrylate | $H_2C=C(CH_3)-C(=O)-OCH_2-C(CH_3)_2-CH_2-O-C(=O)-C(CH_3)=CH_2$ |

TABLE 1-continued

List of acrylate monomers

| Monomer name | Monomer structure |
| --- | --- |
| Trimethylolpropane benzoate diacrylate | |
| Trimethylolpropane ethoxylate(1 EO/OH) methyl | |
| Tricyclo[5.2.1.0$^{2,6}$]-decanedimethanol diacrylate | |
| Neopentyl glycol ethoxylate diacrylate | |
| Trimethylolpropane triacrylate | |
| 1,6-Hexanediol ethoxylate diacrylate M$_n$ ~314 | |
| 2,2,3,3,4,4,5,5 octafluoro 1,6 hexanediol diacrylate | |
| Poly(propylene glycol) diacrylate | n = 7 |
| 1,9 nonanediol diacrylate | |

The acrylates listed in Table 1 may be synthesized as known in the art or obtained from a commercial vendor, such as Polysciences, Inc., Sigma Aldrich, Inc., and Sartomer, Inc.

Figure 1B:
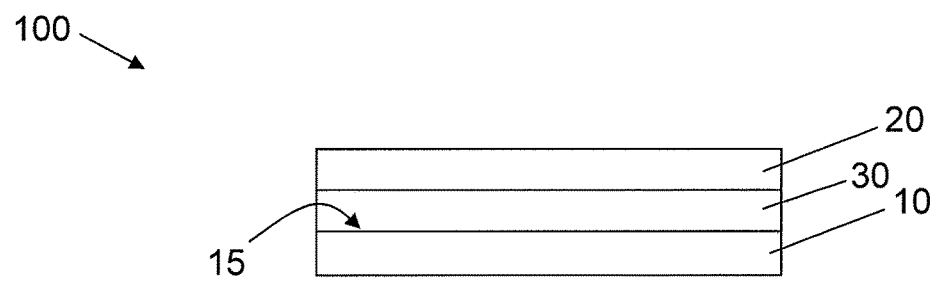

As shown in FIG. 1B, an intermediate layer 30 may be disposed between surface 15 of base material 10 and the synthetic polymer coating 20. Intermediate layer 30 may be configured to improve binding of coating 20 to substrate 10, to facilitate monomer spreading, to render portions of the surface 10 that are uncoated cytophobic to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with a silane molecule or an epoxy coating. For various polymer base materials 10 it may be desirable to provide an intermediate layer 30 of polyamide, polyimide, polypropylene, polyethtylene, or polyacrylate. While not shown, it will be understood that synthetic polymer coating 20 may be disposed on a portion of intermediate layer 30. It will be further understood that intermediate layer 30 may be disposed on a portion of base material 10.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency (RF) and microwave plasmas both primary and secondary, dielectric barrier discharge, and corona discharge generated in molecular or mixed gases including air, oxygen, nitrogen, argon, carbon dioxide, nitrous oxide, or water vapor.

Synthetic polymer coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. While the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Higher degrees of cross-linking may result in reduced waste product and reduced cell toxicity.

Figure 2A:
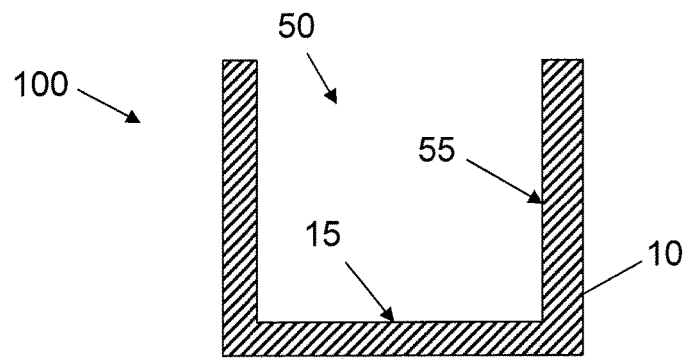
FIGS. 2A-C are schematic diagrams of cross sections of cell culture articles having a well. Uncoated (FIG. 2A); coated surface (FIG. 2B); and coated surface and side walls (FIG. 2C).
Figure 2B:
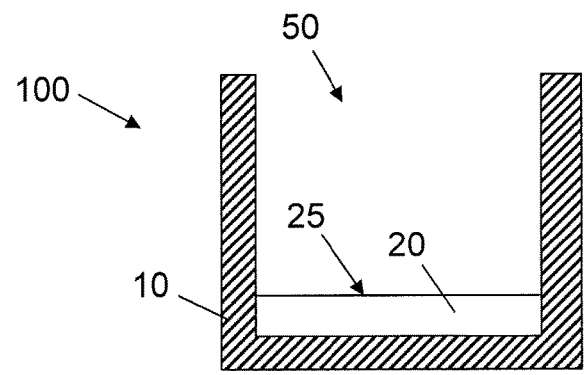
Figure 2C:
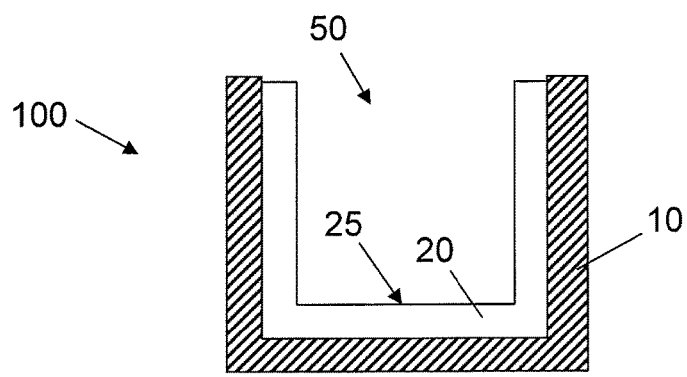

Article 100, in numerous embodiments, is cell culture ware having a well, such as a petri dish, a multi-well plate, a flask, a beaker or other container having a well. Referring now to FIG. 2, article 100 formed from base material 10 may include one or more wells 50. Well 50 includes a sidewall 55 and a surface 15. Referring to FIG. 2B-C, a synthetic polymer coating 20 may be disposed on surface 15 or sidewalls 55 (or, as discussed above with regard to FIG. 1 one or more intermediate layer 30 may be disposed between surface 15 or sidewall 55 and synthetic polymer coating 20) or a portion thereof.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

2. Coating of Synthetic Polymer Layer

A synthetic polymer layer may be disposed on a surface of a cell culture article via any known or future developed process. Preferably, the synthetic polymer layer provides a uniform layer that does not delaminate during typical cell culture conditions. The synthetic polymer surface may be associated with the base material substrate via covalent or non-covalent interactions. Examples of non-covalent interactions that may associate the synthetic polymer surface with the substrate include chemical adsorption, hydrogen bonding, surface interpenetration, ionic bonding, van der Waals forces, hydrophobic interactions, dipole-dipole interactions, mechanical interlocking, and combinations thereof.

In various embodiments, the base material substrate surface is coated according to the teachings of application Ser. No. 61/062,937, filed Jan. 30, 2008, entitled STEM CELL CULTURE ARTICLE AND SCREENING, which is hereby incorporated herein by reference in its entirety for all purposes to the extent that it does not conflict with the disclosure presented herein.

In numerous embodiments, monomers are deposited on a surface of a cell culture article and polymerized in situ. In such embodiments, the base material will be referred to herein as the "substrate" on which the synthetic polymer material is deposited. Polymerization may be done in solution phase or in bulk phase.

As many of the monomers identified in Table 1 above are viscous, it may be desirable to dilute the monomers in a suitable solvent to reduce viscosity prior to being dispensed on the surface. Reducing viscosity may allow for thinner and more uniform layers of the synthetic polymer material to be formed. One of skill in the art will be able to readily select a suitable solvent. Preferably the solvent is compatible with the material forming the cell culture article and the monomers. It may be desirable to select a solvent that is non-toxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In additional embodiments, it may be desirable to select solvents which do not interact with the substrate. Further, it may be desirable that the solvent be readily removable without harsh conditions, such as vacuum or extreme heat. Volatile solvents are examples of such readily removable solvents. As described in application Ser. No. 61/062,937, ethanol may be a particularly suitable solvent when it is desired to remove solvent prior to polymerization.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol solvent to provide a composition having between about 0.1% and about 50% monomer, or from about 0.1% to about 10% monomer by volume. The monomers may be diluted with solvent so that the polymer layer 20 achieves a desired thickness. As discussed above, if the deposited monomers are too thick, an uneven surface may result. As described in further details in the Examples, uneven surfaces may be observed when the monomer-solvent composition is deposited on a surface 15 of a well 50 at a volume of greater than about 8 microliters per square centimeter of the surface 15. In various embodiments, the monomer-solvent compositions are deposited on a surface 15 of a well 50 in a volume of about 7 microliters or less per square centimeter of the surface 15. For example, the monomer-solvent compositions may be deposited on a surface 15 of a well 50 in a volume of about 5 microliters or less per square centimeter of the surface 15, or about 2 microliters or less per square centimeter of the surface 15.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

In various embodiments, synthetic polymer surface is deposited on a surface of an intermediate layer that is associated with the base material via covalent or non-covalent interactions, either directly or via one or more additional intermediate layers (not shown). In such embodiments, the intermediate layer will be referred to herein as the "substrate" onto which the synthetic polymer surface is deposited.

In various embodiments, the surface of the base material is treated. The surface may be treated to improve binding of the synthetic polymer surface to the base material surface, to facilitate monomer spreading on the base material surface, or the like. Of course, the base material may be treated for similar purposes with regard to an intermediate layer. In various embodiments, the surface is corona treated or vacuum plasma treated. High surfaces energy obtainable from such treatments may facilitate monomer spreading and uniform coating. Examples of vacuum plasma treatment that may be employed include microwave vacuum plasma treatments and radio frequency vacuum plasma treatments. The vacuum plasma treatments may be performed in the presence of reactive gases, such as oxygen, nitrogen, ammonia or nitrous oxide.

To form the synthetic polymer surface, one or more monomers presented in Table 1 above are polymerized. If one monomer is used, the polymer will be referred to as a homopolymer of the monomer. If two or more different monomers are used, the polymer will be referred to as a copolymer of the monomers. The monomers employed may be monofunctional, difunctional, or higher-functional. When two or more monomers are used, the ratio of the monomers may be varied. In various embodiments, two monomers are used and the ratio, by volume of the first monomer to the second monomer ranges from between about 5:95 to about 95:5. For example, the ratio of the first monomer to the second monomer ranges from between about 10:90 to about 90:10, about 20:80 to about 80:20, from about 30:70 to about 70:30. In some embodiments, the ratio of the first monomer to the second monomer is about 50:50, 30:70, or 10:90. It will be understood that the degree of cross-linking of the polymer may be controlled by varying the concentration of monomers or the ratios of difunctional or higher-functional monomers to monofunctional monomers. Increased concentrations of difunctional or higher-functional monomers will increase the degree of cross-linking in the chains.

In addition to the monomers that form the polymer layer, a composition forming the layer may include one or more additional compounds such as surfactants, wetting agents, photoinitiators, thermal initiators, catalysts, activators, and cross-linking agents.

Any suitable polymerization initiator may be employed. One of skill in the art will readily be able to select a suitable initiator, e.g. a radical initiator or a cationic initiator, suitable for use with the monomers listed in Table 1. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl group include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photo sensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

In various embodiments where the monomers are diluted in solvent before being deposited on the substrate surface, the solvent is removed prior to polymerizing. The solvent may be removed by any suitable mechanism or process. As described in application Ser. No. 61/062,937, it has been found that removal of substantially all of the solvent prior to curing, allows for better control of curing kinetics and the amount of monomer converted. When conversion rates of the monomers are increased, waste generation and cytotoxicity are reduced.

Whether polymerized in bulk phase (substantially solvent free) or solvent phase, the monomers are polymerized via an appropriate initiation mechanism. Many of such mechanisms are well known in the art. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity.

The cured synthetic polymer layer may be washed with solvent one or more times to remove impurities such as unreacted monomers or low molecular weight polymer species. In various embodiments, the layer is washed with an ethanol solvent, e.g. 70% ethanol, greater than about 90% ethanol, greater than about 95% ethanol, or greater than about 99% ethanol. Washing with an ethanol solvent may not only serve to remove impurities, which may be cytotoxic, but also can serve to sterilize the surface prior to incubation with cells.

3. Incubating Cells on Synthetic Polymer Layer

Stem cell-derived OPCs may be cultured on a synthetic polymer layer, as described above, according to any suitable protocol. As used herein, "stem cell derived OPC" means an OPC obtained from differentiation of a stem cell. In some embodiments, the stem cells are multipotent, totipotent, or pluripotent stem cells. The stem cells may be present in an organ or tissue of a subject. In numerous embodiments, the stem cells are embryonic stem cells, such as human embryonic stem cells. As used herein, "OPC" or "oligodendrocyte progenitor cell" means precursor cells to myelin-forming oligodendrocytes.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

OPCs according to the invention may also be differentiated from induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into OPCs. The iPS cells, like hESC, also form teratomas when injected into immuno-deficient mice, e.g., SCID mice. (Takahashi et al., (2007) Cell 131(5):861; Yu et al., (2007) Science 318:5858).

Stem cell derived OPCs may be obtained by any suitable methods. One way to obtain such cells is described in Zhang et al., "Oligodendrocyte progenitor cells derived from human embryonic stem cells express neurotrophic factors, *Stem Cells and Development,* 15: 943-952 (2006), citing Nistor et al., Human embryonic stem cells differentiate into oligodendrocytes in high purity and mylenate after spinal cord transplantation, Glia 49: 385-396 (2005). Briefly, undifferentiated human embryonic stem cells, such as those derived from the H1 or H7 human embryonic stem cell lines, may be cultured on MATRIGEL-coated plates in mouse embryonic fibroblast (MEF) conditioned medium (CM) supplemented with about 8 ng/ml fibroblast growth factor-2 (FGF-2) or in a chemically defined medium, such as X-VIVO 10 from Cambrex, supplemented with about 80 ng/ml FGF-2 and 0.5 ng/ml transforming growth factor-β1 (TGF-β1). To induce differentiation, the protocol described by Nistor et al. may be employed. Briefly, the human embryonic stem cells may be collagenase digested, scraped, and cultured in defined medium supplemented with insulin, transferrin, progesterone, putrescin, selenium, triiodothyroidin and B27 for 28 days on an ultra-low-attachment plate. The cells may then be cultured in the defined medium for an additional 14 days on growth-factor reduced MATRIGEL. The cells may then be treated with FGF-2, epidermal growth factor (EGF) and all-trans retinoic acid on specified days during differentiation. Differentiation may occur over a number of days, such as 42 days. Of course, any other suitable method may be employed.

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, conditioned media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature $CO_2$ and $O_2$ levels, growth medium, and the like, will depend on the nature of the cells being cultured and can be readily modified. The amount of time that the cells are incubated on the surface may vary depending on the cell response being studied or the cell response desired.

Any suitable method may be used, if desired, to confirm that the stem cell derived OPCs are indeed OPCs or that the stem cells employed have successfully differentiated into OPCs. For example, the presence of certain OPC-selective markers may be investigated. Such markers include Nestin, Oligo1, platelet derived growth factor receptor alpha (PDGFRα) and NG2. Antibodies to such markers may be used in standard immunocytochemical or flow cytometry techniques. In addition or alternatively, cellular morphology or production of growth factors detectable in the medium may be evaluated. For example, cultured OPCs may produce one or more of activin A, HGF, midkine, and TGF-β2, which may be detectable in the culture medium via standard assays, such as ELISA.

The cultured stem cell derived OPCs may be used for any suitable purpose, including investigational studies in culture, in animals, for developing therapeutic uses, or for therapeutic purposes. One potential therapeutic or investigational purpose is repairing damage due to spinal cord injury.

In the following, non-limiting examples are presented, which describe various embodiments of the articles and methods discussed above.

EXAMPLES

Example 1: Identification of Acrylic Coating Surfaces Suitable for Culturing Stem Cell Derived OPCs in a Chemically Defined Medium 1. Coating Preparation Acrylic coating surfaces were prepared from homomonomers or copolymers of various acrylate monomers. For copolymers two different acrylate monomers were used. A total of 24 homopolymer and 552 copolymer combinations were applied in wells. Briefly, the monomers were diluted in ethanol, and IRGACURE 819 photoinitiator to the ratio of 1:9:0.01 (monomer[volume]/ethanol[volume]/photoinitiator [weight]) to prepare the formulation. For copolymers, two different monomers were mixed with the volume ratio of 70:30 or 30:70. In copolymer formulation, total monomers [volume]/ethanol[volume]/photoinitiator[weight] still remain the ratio of 1:9:0.01. The formulations were placed in a well of a plasma treated cyclic olefin copolymer 96 well plates (provided by Corning Life Science development group) at a volume of 5 µL using BioTek Precession Microplate Pipetting System. Each well received a predetermined homopolymer or copolymer combination, with some wells being coated with MATRIGEL as a positive control. For the wells coated with acrylate monomers, the ethanol solvent was removed by evaporation at room temperature for 3 hr, which removes >99% of the ethanol. The coatings were then cured with 13 mW/cm$^2$ pulsed (100 Hz) UV light (Xenon RC-801) for 1 min in N$_2$ purged box (with fused silica window). After curing, a washing step was taken. Briefly, the surface in each well of 96-well plates was incubated with 200 µL of >99% ethanol for 1 hr followed by 200 µL of water for over night to move potential extractables. Finally the surfaces were air dried before sterilization.

2. Cell Preparation and Assays

For hESC-derived OPC, H1 hESC colonies were detached using 200 U/ml collagenase IV and transferred to Corning ultra-low-adhesion (ULA) plates to allow the formation of embryoid bodies (EBs). To induce neural differentiation, EBs were treated with epidermal growth factor (EGF), FGF-2 (fibroblast growth factor-2) and retinoic acid (RA) for 9 days following by 18 days treatment with EGF only. (Base medium: defined medium supplemented with insulin, transferrin, progesterone, putrescin, selenium, triiodothyroidin (Sigma), and B27 (Invitrogen)).

At this point two different acrylate re-plating schedules were tested: In the first protocol, on day 28, EBs were re-plated on different acrylic surfaces in 96-well plate or on MATRIGEL-coated wells as positive control. Seven days later (day 35), cells were fixed with 4% PFA. In the second protocol, on day 28, EBs were re-plated on MATRIGEL, cultured for 7 days and then (day 35) re-plated on different acrylic surfaces in 96-well plate or on MATRIGEL-coated wells as positive control. Seven days later (day 42), cells were fixed with 4% PFA.

Cells from the both protocols were immunostained for OPC-specific markers, Nestin, Olig1, and counterstained with 4'-6-Diamidino-2-phenylindole DAPI (nuclear stain).

After scanning each plate with ArrayScan, the following quantitative analyses were performed for the each surface: 1) TNC: total number of cells, based on DAPI positive cell number, 2) TNO: total number of OPC, based on olig1-positive cells.

3. Results

Figure 3A:
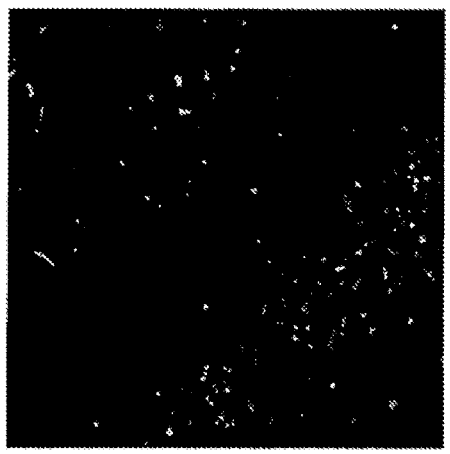
FIGS. 3A-C are florescence images of immunostained hES cell-derived OPCs after replating on acrylate coating surface 123-2 (FIG. 3A) and 95-2 (FIG. 3B), and positive control surface Matrigel® (FIG. 3C) between 28-day and 35-day. OPCs derived from human ES cells were immunostained for the OPC marker, Olig1 (green) and nestin (red).
Figure 3B:
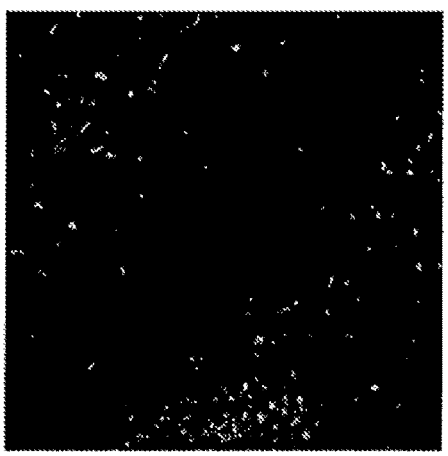
Figure 3C:
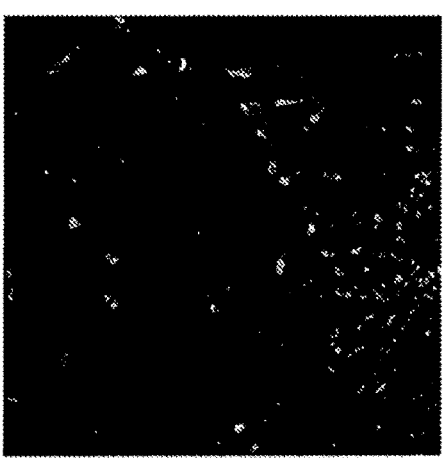
Figure 4A:
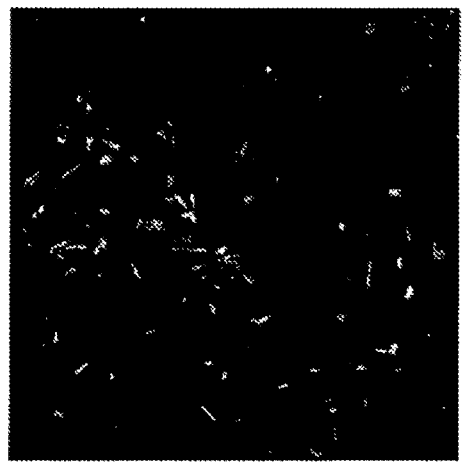
FIGS. 4A-C are fluorescence images of immunostained hES cell-derived OPCs after replating on acrylate coated surface 123-2 (FIG. 4A), 122-3 (FIG. 4B) and Matrigel® (FIG. 4C) between 28-day and 35-day as well as between 35-day and 42-day. OPCs derived from human ES cells were immunostained for the OPC marker, Olig1 (green) and nestin (red).
Figure 4B:
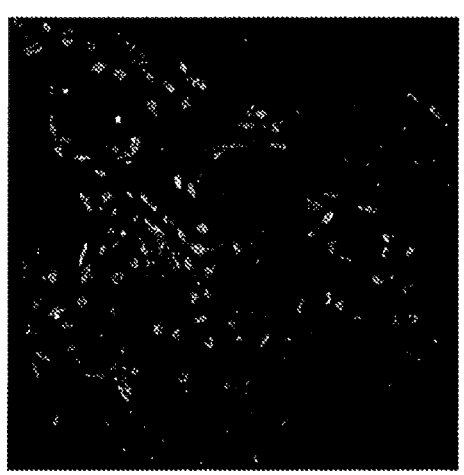
Figure 4C:
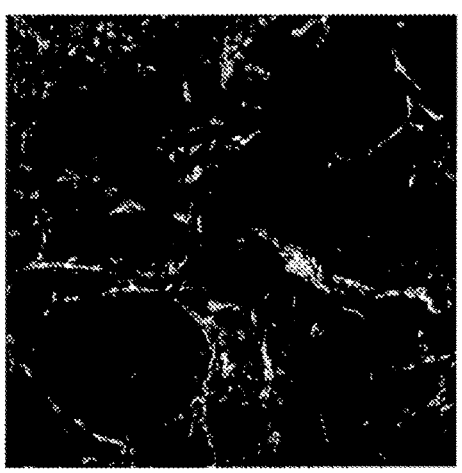
Figure 5A:
FIGS. 5A-F are fluorescence images of hES cell-derived OPCs on Matrigel® (FIG. 5A) and on acrylate coated surfaces 22-2 (FIG. 5B), 22-3 (FIG. 5C), 133-4 (FIG. 5D), 24-10 (FIG. 5E), and 72-2 (FIG. 5F).
Figure 5B:
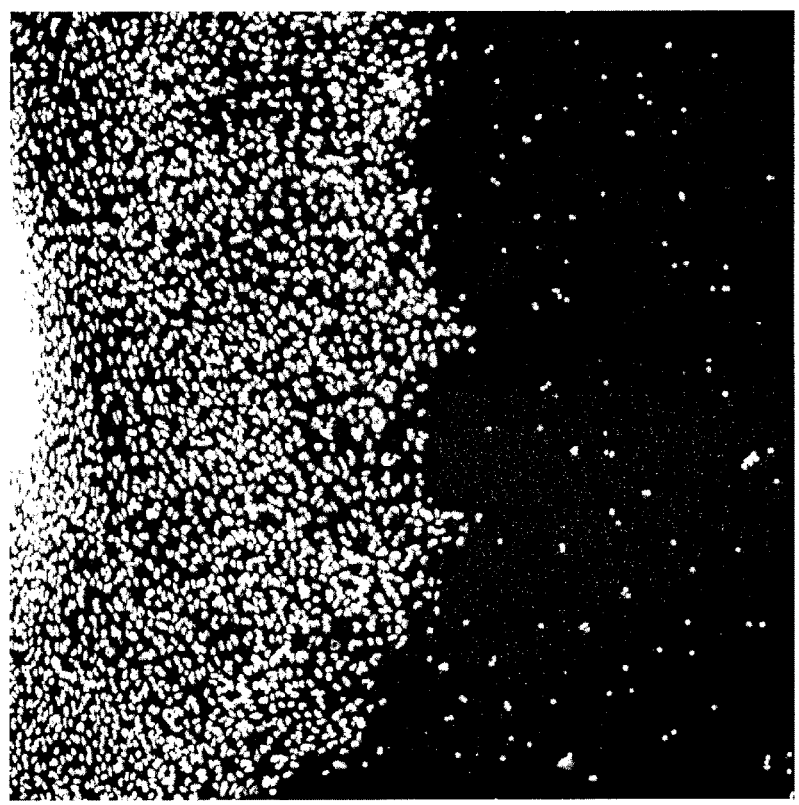
Figure 5C:
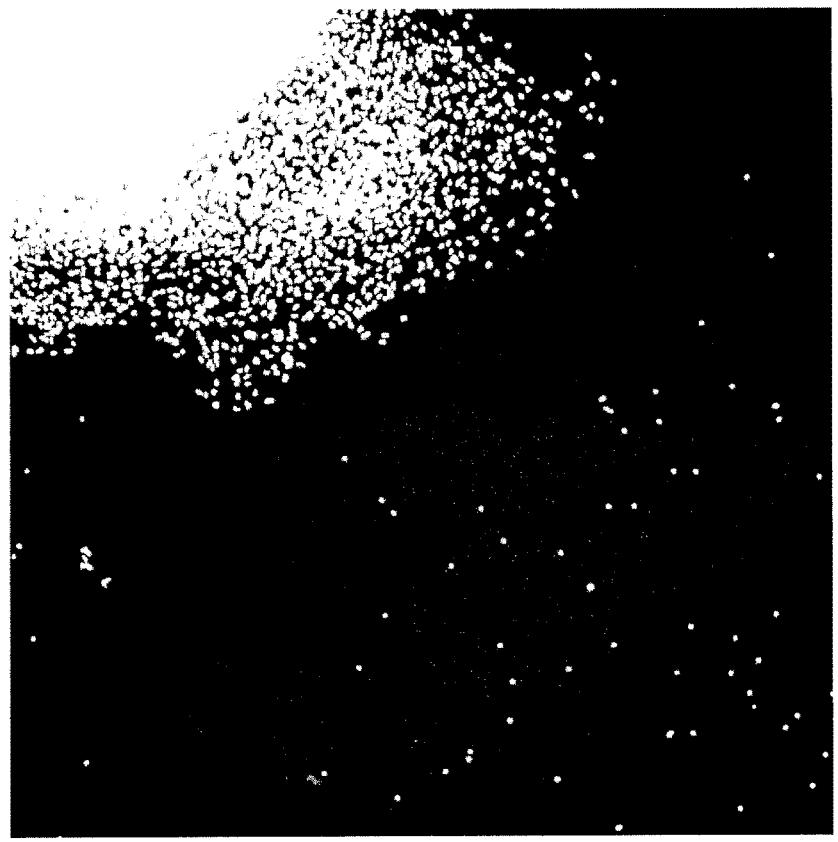
Figure 5D:
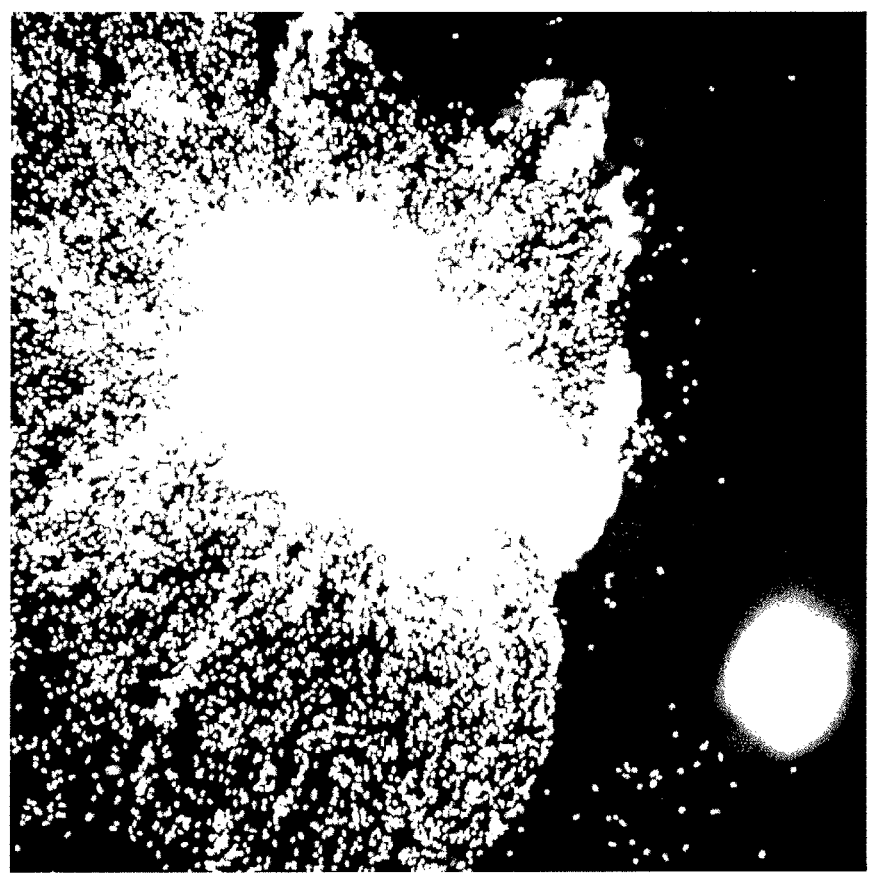
Figure 5E:
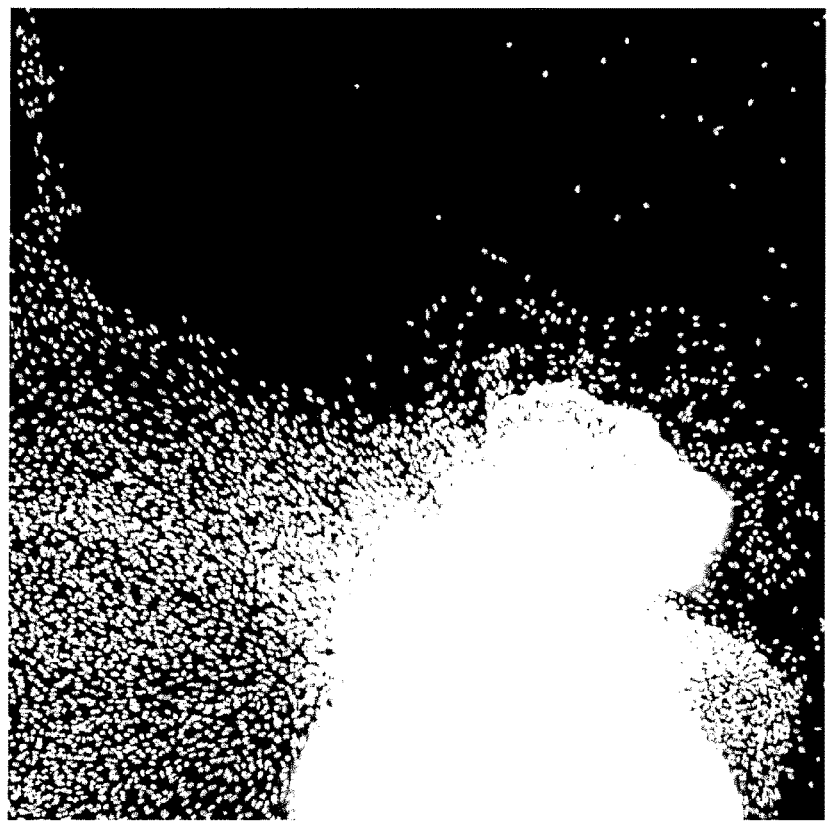
Figure 5F:
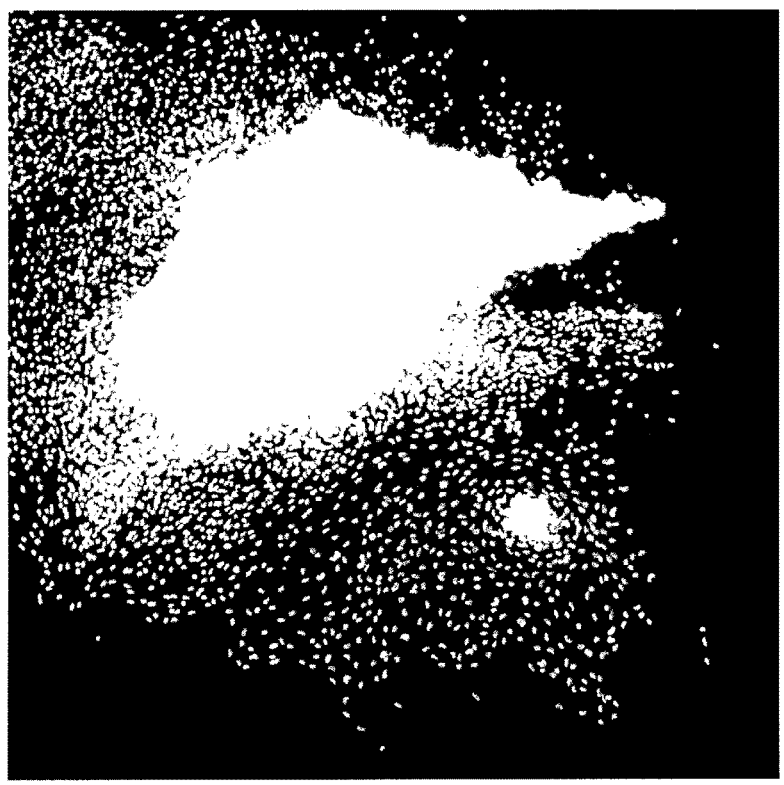

It was found that only a small portion of the tested surfaces supported attachment and cell outgrowth from EBs in chemically defined medium. FIG. 3 are fluorescence images of immunostained hES cell-derived OPC after re-plating on selected acrylate coated surfaces and positive control Matrigel surface between 28-day and 35-day for differentiation. FIG. 4 are fluorescence images of immunostained hES cell-derived OPC after two re-platings on selected acrylate coated surfaces and positive control Matrigel surface between 28-day and 35-day, as well as between 35-day and 42-days for differentiation. The immunostaining images showed that differentiated cells expressed the OPC markers on some acrylate coating surfaces. The staining of the cells grown on the acrylate surfaces was similar to the staining observed in the cells grown on the Martigel control surface. Examples of the coating surfaces which supported differentiated human OPCs in chemically defined medium are listed in Table 2, where the volume ratio of monomer (1) to monomer (2) is 70:30.

TABLE 2

Example compositions of acrylic polymers which support the culture of hES cell derived OPCs in chemically defined medium.

| Polymer ID | Monomer (1) | Monomer (2) |
|---|---|---|
| 95-1 | Tetra(ethylene glycol) diacrylate | |
| 27-1 | Tetra(ethylene glycol) diacrylate | Neopentyl glycol ethoxylate diacrylate |
| 123-1 | Glycerol dimethacrylate | Tetra(ethylene glycol) diacrylate |
| 123-2 | Glycerol dimethacrylate | Tri(ethylene glycol) dimethacrylate |
| 22-1 | Glycerol dimethacrylate | Di(ethylene glycol) dimethacrylate |
| 22-2 | Glycerol dimethacrylate | Tetraethylene glycol dimethacrylate |
| 22-3 | Glycerol dimethacrylate | 1,6-Hexanediol propoxylate diacrylate |

TABLE 2-continued

Example compositions of acrylic polymers which support the culture of hES cell derived OPCs in chemically defined medium.

| Polymer ID | Monomer (1) | Monomer (2) |
|---|---|---|
| 24-10 | Glycerol dimethacrylate | 1,6-Hexanediol ethoxylate diacrylate |
| 28-2 | Tri(ethylene glycol) dimethacrylate | Trimethylolpropane triacrylate |
| 28-10 | 1,4-Butanediol dimethacrylate | 1,9 nonanediol diacrylate |
| 36-4 | 1,6-Hexanediol diacrylate | Tricyclo[5.2.1.0$^{2,6}$]decanedimethanol diacrylate |
| 36-5 | 1,6-Hexanediol diacrylate | 1,6-Hexanediol ethoxylate diacrylate |
| 36-6 | 1,6-Hexanediol diacrylate | Neopentyl glycol ethoxylate diacrylate |
| 39-6 | Neopentyl glycol propoxylate (1PO/OH) diacrylate | Neopentyl glycol ethoxylate diacrylate |
| 133-4 | Di(ethylene glycol) dimethacrylate | Neopentyl glycol diacrylate |
| 47-4 | Di(ethylene glycol) dimethacrylate | Tricyclo[5.2.1.0$^{2,6}$]decanedimethanol diacrylate |
| 41-9 | Tetra(ethylene glycol) dimethacrylate | 1,4-Butanediol dimethacrylate |
| 50-6 | Tetra(ethylene glycol) dimethacrylate | Neopentyl glycol ethoxylate diacrylate |
| 51-1 | 1,6-Hexanediol propoxylate diacrylate | Neopentyl glycol ethoxylate diacrylate |
| 49-4 | Neopentyl glycol diacrylate | Tricyclo[5.2.1.0$^{2,6}$]decanedimethanol diacrylate |
| 49-5 | Neopentyl glycol diacrylate | 1,6-Hexanediol ethoxylate diacrylate |
| 52-4 | Neopentyl glycol diacrylate | Poly(propylene glycol) diacrylate |
| 63-3 | Trimethylolpropane ethoxylate (1 EO/OH) methyl diacrylate | 2,2,3,3,4,4,5,5 octafluoro 1,6 hexanediol diacrylate |
| 71-1 | Neopentyl glycol ethoxylate diacrylate | Di(ethylene glycol) dimethacrylate |
| 65-9 | Trimethylolpropane triacrylate | 1,4-Butanediol dimethacrylate |
| 71-6 | Trimethylolpropane triacrylate | Di(ethylene glycol) dimethacrylate |
| 71-10 | Trimethylolpropane triacrylate | Neopentyl glycol diacrylate |
| 74-6 | Trimethylolpropane triacrylate | Neopentyl glycol dimethacrylate |
| 72-2 | 2,2,3,3,4,4,5,5 octafluoro 1,6 hexanediol diacrylate | Tetra(ethylene glycol) dimethacrylate |
| 72-5 | 2,2,3,3,4,4,5,5 octafluoro 1,6 hexanediol diacrylate | Neopentyl glycol diacrylate |
| 72-9 | Poly(propylene glycol) diacrylate | Glycerol 1,3-diglycerolate diacrylate |

FIGS. 5A-F show images taken from micrographs of hESC derived OPCs growing on Matrigel™ as a positive control and selected embodiments of surfaces of the present invention; 22-2 (B), 22-3 (C), 133-4 (D), 24-10 (E), and 72-2 (F). FIGS. 5A-F show nuclear staining on hESC derived OPCs on Matrigel or the above-referenced embodiments of surfaces of the present invention stained with Hoecst nuclear stain. FIGS. 5A-F illustrate that embodiments of surfaces of the present invention provide suitable surfaces to support adhesion and growth of hESC derived OPCs in chemically defined medium. For other tested homopolymers and copolymer combinations, that is those combinations that are not listed in Table 2 above, no EB attachment to the surface or cell outgrows from the EBs was observed.

Thus, embodiments of SYNTHETIC SURFACES FOR CULTURING STEM CELL DERIVED OLIGODENDROCYTE PROGENITOR CELLS are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A method for culturing human pluripotent stem cell-derived oligodendrocyte progenitor cells, comprising depositing a suspension comprising the human pluripotent stem cell-derived oligodendrocyte progenitor cells on a polymer material, and culturing the deposited human pluripotent stem cell-derived oligodendrocyte progenitor cells in a cell culture medium, wherein the polymer material comprises a diacrylate or a dimethacrylate.

2. The method of claim 1, wherein the dimethacrylate is glycerol dimethacrylate.

3. The method of claim 1, wherein the diacrylate is 1,6-hexanediol diacrylate.

4. The method of claim 1, wherein the diacrylate is tetra(ethylene glycol) diacrylate.

5. The method of claim 1, wherein the polymer material comprises about 70% glycerol dimethacrylate.

6. The method of claim 1, wherein the human pluripotent stem cells are human sells induced pluripotent stem (iPS) cells.

7. The method of claim 1, wherein the human pluripotent stem cells are human embryonic stem (hES) cells.

8. The method of claim 1, wherein the cell culture medium is a chemically defined medium.

* * * * *